(12) United States Patent
Poehler et al.

(10) Patent No.: US 10,473,583 B2
(45) Date of Patent: Nov. 12, 2019

(54) SPECTROSCOPIC MEASURING DEVICE AND METHOD TO DETERMINE CONCENTRATIONS OF POLLUTANTS

(71) Applicant: AIRYX GMBH, Eppelheim (DE)

(72) Inventors: Denis Poehler, Eppelheim (DE); Martin Horbanski, Heidelberg (DE); Ulrich Platt, Dossenheim (DE)

(73) Assignee: AIRYX GMBH, Eppelheim (DE)

( * ) Notice: Subject to any disclaimer, the term of this patent is extended or adjusted under 35 U.S.C. 154(b) by 0 days.

(21) Appl. No.: 15/748,923

(22) PCT Filed: Aug. 1, 2016

(86) PCT No.: PCT/EP2016/068344
§ 371 (c)(1),
(2) Date: Aug. 21, 2018

(87) PCT Pub. No.: WO2017/017284
PCT Pub. Date: Feb. 2, 2017

(65) Prior Publication Data
US 2019/0011354 A1   Jan. 10, 2019

(30) Foreign Application Priority Data

Jul. 30, 2015   (EP) .................................. 15179088

(51) Int. Cl.
*G01N 21/31*   (2006.01)
*G01J 3/42*   (2006.01)
(Continued)

(52) U.S. Cl.
CPC ................ *G01N 21/31* (2013.01); *G01J 3/28* (2013.01); *G01J 3/42* (2013.01); *G01N 21/274* (2013.01);
(Continued)

(58) Field of Classification Search
CPC .. G01N 21/31; G01N 21/274; G01N 33/0006; G01J 3/42
(Continued)

(56) References Cited

U.S. PATENT DOCUMENTS 3,588,496 A * 6/1971 Snowman ............ G01N 21/031
250/343
3,860,818 A * 1/1975 Stalder .................. G01N 21/85
250/343

(Continued)

OTHER PUBLICATIONS

Hoch et al., "An instrument for measurements of BrO with LED-based Cavity-enhanced Differential Optical Absorption Spectroscopy", Atmospheric Measurement Techniques, vol. 7, No. 1, Jan. 27, 2014, Germany, pp. 199-214. (Year: 2014).*

(Continued)

*Primary Examiner* — Roy M Punnoose
(74) *Attorney, Agent, or Firm* — Grossmam, Tucker, Perreault & Pfleger, PLLC

(57) ABSTRACT

The invention relates to a method for determining concentrations of absorbing gases by means of a spectroscopic measuring device, wherein wavelength-dependent measurement values for a light intensity are obtained and a wavelength-dependent measurement value function is represented based on these values. A wavelength-dependent theoretical function is defined, which includes as parameters a calibration parameter and the concentrations. The calibration parameter is defined as a function of a device parameter and a correction parameter that depends on the concentrations. A cycle comprising a sequence of steps is performed several times in a row, wherein in a first step a numerical value for the correction factor is calculated from stipulated assumed values of the concentrations, wherein in a second step the theoretical function is determined using the calculated numerical value, wherein in a third step values for the (Continued)

concentrations are obtained by a curve adjustment calculation between the theoretical function determined in the second step and the measurement value functions and are stipulated as new assumed values. The assumed values obtained in the third step of the last cycle are output as new measured values.

15 Claims, 3 Drawing Sheets

(51) Int. Cl.
G01N 21/27 (2006.01)
G01J 3/28 (2006.01)
G01N 33/00 (2006.01)
G01N 21/03 (2006.01)

(52) U.S. Cl.
CPC ....... *G01N 33/0006* (2013.01); *G01N 21/031* (2013.01); *G01N 2021/3125* (2013.01); *G01N 2021/3129* (2013.01); *G01N 2021/3137* (2013.01)

(58) Field of Classification Search
USPC ........................................................ 356/437
See application file for complete search history.

(56) References Cited

U.S. PATENT DOCUMENTS

| 5,047,639 | A | * | 9/1991 | Wong | G01N 21/39 250/341.1 |
| 5,750,999 | A | * | 5/1998 | Fox | G01N 31/005 250/343 |
| 2008/0179530 | A1 | * | 7/2008 | Liu | G01N 21/274 250/343 |
| 2015/0338342 | A1 | * | 11/2015 | Muramatsu | G01N 21/39 356/409 |
| 2017/0097301 | A1 | * | 4/2017 | Lefebvre | G01N 21/274 |
| 2018/0275049 | A1 | * | 9/2018 | Mazzotti | G01N 21/3504 |

OTHER PUBLICATIONS

English translation of International Search Report dated May 10, 2016, received in corresponding PCT Application No. PCT/EP2016/068344.

English translation of the Written Opinion dated Dec. 1, 2017, received in corresponding PCT Application No. PCT/EP2016/068344.

Hoch et al., "An instrument for measurements of BrO with LED-based Cavity-enhanced Differential Optical Absorption Spectroscopy", Atmospheric Measurement Techniques, vol. 7, No. 1, Jan. 27, 2014, Germany, pp. 199-214.

Platt et al., "Broadband Cavity Enhanced Differential Optical Absorption Spectroscopy (CE-DOAS)—applicability and corrections", Atmospheric Measurement Techniques, No. 2, Nov. 16, 2009, Germany, pp. 713-723.

University of Heidelberg, "Advanced Lab Course Cavity-Enhanced-DOAS", Aug. 5, 2014, pp. 1-74, Germany.

* cited by examiner

SPECTROSCOPIC MEASURING DEVICE AND METHOD TO DETERMINE CONCENTRATIONS OF POLLUTANTS

FIELD

The invention relates to a method for determining concentrations of absorbing gases measured in a gas mixture using a spectroscopic measuring device. The invention also relates to a spectroscopic measuring device.

BACKGROUND

Conventionally, spectroscopic measuring devices are used to determine concentrations of absorbing gases in a measured gas mixture. For example, the gas mixture to be measured can be ambient air in which the concentrations of absorbing gases shall be determined. Absorbing gases are the general term for gaseous compounds absorbing light in a particular wavelength range. For example, trace gases such as NO, $NO_2$, $NO_3$ or $O_3$ are covered by the term "absorbing gases". Particularly the concentrations of such trace gases are frequently measured using corresponding spectroscopic measuring devices. The basic principle of all spectroscopic measuring devices is that each absorbing gas, due to its characteristic molecule structure, has a particular absorption structure when excited by light. If a molecule of such an absorbing gas is excited by a light source emitting light with a wavelength-dependent light intensity over a particular spectral width, i.e. a particular wavelength range, this molecule will absorb a portion of this light corresponding to its specific absorption spectrum, wherein the portion of the absorbed light depends on the wavelength. Accordingly, the absorption spectrum defines the wavelength-dependent absorption characteristic of an absorbing gas regarding the absorption of light. When light from a light source is emitted to a gas mixture whereby the light travels a light path in the gas mixture, then according to the specific absorption spectrum of the absorbing gas more light intensity is absorbed if the light hits more molecules of the absorbing gas on its light path. The light intensity measured after the light emitted from a light source has traveled a certain light path in a particular gas mixture with a particular absorbing gas, depends accordingly on both the path length of the light path and the concentration of the absorbing gas in the gas mixture. Mathematically, this basic principle can be described using the Beer-Lambert law: $I=I_0*\exp[-\sigma*x*L]$, where I is the light intensity after it traveled the light path in the gas mixture, $I_0$ is the light intensity emitted from the light source to the gas mixture, $\sigma$ is the absorption cross section of the trace gas, x is the concentration of the trace gas and L is the path length of the light path. The absorption cross section of a trace gas of course depends on the wavelength and precisely represents the absorption spectrum of a trace gas.

In the light of this basic principle, conventional spectroscopic measuring devices are always designed as an assembly in which light emitted from a light source travels a predetermined or determinable light path, whereat the end of the light path a detector is arranged which can measure the light intensity. For the implementation of spectroscopic measuring devices various, very different options are known. For example, there are spectroscopic measuring devices in which the light path and hence also the path length of the light path is geometrically fixed by a geometric arrangement of mirrors between a starting point and a destination point. In order to guarantee high measuring accuracy, spectroscopic measuring devices are known having a geometrically fixed light path of several kilometers length. Spectroscopic measuring devices with a measuring cell that comprises an optical resonator follow a completely different approach. The optical resonator is located in the measuring cell and comprises a mirror arrangement to reflect light within the mirror arrangement as often as possible. With such a setup, the light path is not geometrically predefined, but depends for example on the reflectivity of the mirror arrangement and on the absorption of light inside the measuring cell. The higher the reflectivity of the mirror assembly and the lower the absorption, the longer the light path. The absorption can be caused for example by components of the gas mixture, such as the contained trace gases, and/or by the absorption behavior of the mirror arrangement. In such measuring devices comprising an optical resonator, the light intensity coupled out from the measuring cell is measured by a detector. The uncoupling can be accomplished for example using a partially transparent beam splitter in the measuring cell or a partially transparent mirror of the mirror arrangement. Since the light path is not geometrically pre-known, calibration measurements are required so that conclusions on the concentration of absorbing gases in the gas mixture provided in the measuring cell can be drawn from a measured light intensity. Through these calibration measurements a value is determined that characterizes the path length of the light path, for example an "average path length", a "reflectivity" of the mirror arrangement or an "average residence time" of the light in the measuring cell. The options described for the characterization of the path length are equivalent and can be converted into each other. In comparison to the above-described exemplary measuring devices with a fixed geometrical light path, measuring devices comprising an optical resonator have the important advantage that due to the multiple reflections in the optical resonator, a light path can be obtained which is sufficiently long to allow a precise measurement of absorbing gases in a gas mixture, even at a small overall size of the resonator and hence the entire spectroscopic measuring device. As a result, such spectroscopic measuring devices are especially suitable also for local, i.e. spatially resolved measurements of absorbing gas concentrations and are also inexpensive and easy to manufacture.

The present invention relates to such described spectroscopic measuring devices comprising an optical resonator and a method for determining concentrations of absorbing gases in a gas mixture using such spectroscopic measuring devices. Hereby the concentrations of the absorbing gases are determined on the basis of wavelength-dependent measurement values of the light intensity output from the detector. Therefore the read out of the wavelength-dependent measurement values is illustrated as a wavelength-dependent shape of the light intensity a wavelength-dependent measurement value function and where a theoretical wavelength-dependent function according to physical laws is defined, in which function the concentrations are included as selectable parameters, wherein the concentrations are determined by a mathematical fitting algorithm between the theoretical function and the measurement value function. The wavelength-dependent measurement value function is directly calculated from the measurement read out values from the detector and reflects a shape of numerical values that merely depend on the wavelength. For example, the wavelength-dependent measurement value function can be directly defined as a shape of the measured light intensity in dependence of the wavelength. For example, the wavelength-dependent function can be defined by each of the read-out wavelength-dependent measurement values for the light intensity being multiplied by a constant factor or added to a constant summand from which a function value is calculated, wherein this function value is represented in dependence of the wavelength as wavelength-dependent measurement value function.

While a suitable measurement value function can be directly obtained from the measurement values using rather simple arithmetic, the formulation of a useful theoretical function and performing a curve fitting calculation turned out to be difficult. Therefore, it should be taken into account that during the curve fitting calculation, always a numerical variation of the concentrations as a freely selectable and thus fitted parameters of the function must be carried out until the theoretical function is sufficiently well approximated in its shape to the measurement value function. Only, when a sufficiently well approximation between the theoretical function and the measurement value function has been achieved by a corresponding selection of the concentrations as fitted parameters of the theoretical function, one can assume that the concentrations determined in the curve fitting calculation in fact reflect the concentrations of the absorbing gases in the gas mixture. For the assessment when the theoretical function is sufficiently well approximated to the measurement value function, methods known in error calculation are applied such as the determination of the root mean square deviation.

To ensure that such a curve fitting calculation can be numerically performed at all, it is required that the theoretical function has a dependency on the concentrations as parameters to be fitted, which is simple enough to perform a sufficiently good approximation of the theoretical function to the measurement value function through a numerical selection of the concentrations. At the same time, however, the theoretical function must describe the physically expected measurement value function as exactly as possible, in accordance with the physical laws. This is where the problem exists in conventional methods for determining the concentrations of the absorbing gases for spectroscopic measuring devices comprising an optical resonator and concerns the present invention.

Because in such spectroscopic measuring devices, a physically expected measurement value function can be exactly described only by means of very complex mathematical functions, since the formulation of corresponding theoretical functions requires that boundary conditions inherent to such spectroscopic measuring devices are taken into account. On the one hand, the measured light intensity is dependent on the concentration of the absorbing gases and the average path length the light travels inside the measuring cell. The longer the light path at a constant concentration of the absorbing gases, the stronger the absorption in the measuring cell and lower the measured light intensity. On the other hand, the light path depends on both the state of the measuring device (e.g. orientation of the mirror assembly of the resonator and reflectivity of the mirrors, i.e. in particular also contamination of the mirrors) and also the concentrations of the absorbing gases themselves, since the more light is absorbed in the measuring cell, i.e. the greater the concentrations of the absorbing gases, the shorter becomes the average path length. Moreover, the measured light intensity also depends on the properties of the detector that can typically be represented by an instrument function, which characterizes the detector and the entire spectroscopic measuring device. This dependency of the spectroscopic measuring device of instrument functions is relevant for the physically correct presentation of the theoretical function, since both the absorber structures of many absorbing gases and also the properties of the spectroscopic measuring device (especially the reflectivity of the mirrors of the resonator) very strongly depend on the wavelength. Accordingly, a physically correct representation of the theoretical function initially requires a formulation of the expected measurement value function according to physical laws concerning the travel of the light, i.e. the light path, in the measuring cell and thereafter a convolution of this formulation with the instrument function in order to take account of the measuring properties of the measuring device, especially the detector of the measuring device.

In view of the above-described difficulties in the formulation of a physically exact and yet numerically adjustable function, various approximations have been made in state of the an applications in order to achieve a theoretical function that can be used for curve fitting calculation with the measurement value function. One common approach is to define the measurement value function as $$M(\lambda) = \frac{I_0(\lambda)}{I(\lambda)} - 1$$

and the theoretical function as $$T(\lambda) = L_0(\lambda) * \sum_i \varepsilon_i(\lambda),$$

where $I_0(\lambda)$ is the wavelength-dependent shape of an initial light intensity, $I(\lambda)$ is the wavelength-dependent shape of the light intensity resulting from the measurement values during the measurement for determining the concentrations, $L_0$ is a device path length and $\varepsilon_i$ represents the extinction coefficients of the i different absorbing gases. Here $\varepsilon_i$ is frequently expressed as $x_i * \sigma_i$, where $x_i$ is the concentration of a particular one of the i different assumed absorbing gases and $\sigma_i$ is the absorption cross section of the particular absorbing gas known from literature. In common methods using this approximation and performing the fitting calculation where $M(\lambda)$ is set equal to $T(\lambda)$, $I_0(\lambda)$ and $L_0$ are initially determined in calibration measurements. $I_0(\lambda)$ is the initial light intensity measured by the detector when "zero air" is arranged in the measuring cell. Normally, preferably clean air is used as zero air, for example ambient air that has been filtered by aerosol filters for the removal of scattering aerosols and/or by additional filters for the removal of absorbers. For example, $N_2$, $O_2$ or a $N_2$-$O_2$ mixture can also be used as zero air. Different calibration measurements and various methods for performing such calibration measurements are known for the determination of $L_0$. According to one method, an average path length of the light path in the measuring cell is determined $L_0(\lambda)$ by flooding the measuring cell with helium for a first measurement and with zero air for a second measurement. In both measurements, the light intensity is measured at the exit of the measuring cell. As it can be assumed that the differences between the light intensities measured in the first and the second measurements are largely based on a different Rayleigh scattering in air and helium, which respectively depends on the Rayleigh scattering cross section and hence on the molecule size in air or helium, an average path length of the light path and thus the device path length $I_0(\lambda)$ can be obtained from:

$$L_0(\lambda) = \frac{\frac{I_{Luft}(\lambda)}{I_{He}(\lambda)} - 1}{\varepsilon_{He}(\lambda) - \varepsilon_{Luft}(\lambda)},$$

where $I_{Luft}$ is the measured light intensity when flushing the measuring cell with zero air, $I_{He}$ is the measured light intensity when flushing the measuring cell with helium, and $\varepsilon_{He}$ and $\varepsilon_{Luft}$ are the Rayleigh extinction coefficients, wherein the extinction coefficient is calculable from $\varepsilon = \sigma * n$, where $\sigma$ is the Rayleigh cross section sufficiently documented in the literature and n is the particle number density that can be calculated in good approximation using the ideal gas law at a known pressure and temperature. Another method is to flood the measuring cell with a gas mixture containing a pre-known concentration of a particular trace gas. It is then possible to directly draw a conclusion on the average path length of the light path from the measured light intensity and the known absorption structure of the trace gas and thus determine the device path length. This method, however, can only provide information about the wavelength dependency of the path length of the light path within the wavelength range of the absorption structure of the particular trace gas. If lasers are used as a light source for the spectroscopic measuring device, there is another known method for the calibration measurement in which the decay constant of the light intensity is determined after the laser is switched on or off. The decay constant can be determined by:

$$I(t) = I(t_0) * \exp\left[-\frac{c}{L_0}(t - t_0)\right],$$

wherein I is the measured light intensity, $I_0$ is a particular time (after switch-off), c is the light speed and $L_0$ is an average path length of the light path, i.e. the device path length. The decay constant is expressed as $$\frac{c}{L_0}.$$

The conventional method described for the determination of concentrations of absorbing gases, in which the measurement value function $M(\lambda)$ is set equal with the theoretical function $T(\lambda)$ with the definition $$\frac{I_0(\lambda)}{I(\lambda)} - 1 = L_0(\lambda) * \sum_i \varepsilon_i(\lambda),$$

can only lead to an approximately correct determination of the concentration if 1.) only a relatively low absorption of light occurs in the measuring cell or if the measurement values are measured using a very expensive detector with a very high spectral resolution, i.e. resolution regarding the wavelength, and 2.) the state of the measuring device at the determination of $I(\lambda)$ is identical with the state during the determination of $I_0(\lambda)$, because only then the mathematical approximations that have been performed in the determination of the described relation for performing the curve fitting calculation based on physical laws are correct. In any case, the second condition can be achieved only with considerable effort. Because on the one hand, the properties of the optical assembly of the measuring device, especially the measuring cell, may vary as a consequence of a misalignment, contamination of the mirror assembly or due to misalignment of the lens arrangements so that the measurements of $I_0(\lambda)$ and $I(\lambda)$ must preferably be performed in immediate succession so that the initial measurement of $I_0(\lambda)$ must preferably be performed prior to each new measurement for the determination of concentrations in a gas mixture. On the other hand, for conventionally used light sources, the intensity emitted from the light source considerably varies already within short time intervals. Considering, however, that for applying the described relation, it is an absolutely requirement that the spectroscopic measuring device and particularly also the light source are in the same state to determine the concentration of absorbing gases, thus complex measures must be applied in conventional methods to stabilize the emitted intensity from the light. Such measures are frequently insufficient, on the one hand, and expensive on the otherhand.

Furthermore, conventional methods exist for the determination of concentrations of absorbing gases in which the measurement value function $M(\lambda)$ is represented by $$M(\lambda) = \ln\left(\frac{I_0(\lambda)}{I(\lambda)}\right)$$

and the theoretical function is represented $$T(\lambda) = L_{eff}(\lambda) * \sum_i \varepsilon_i(\lambda) + A,$$

where $M(\lambda)$ is set equal to $T(\lambda)$ performing the curve fitting calculation. In this equation, $L_0(\lambda)$, $I(\lambda)$ and $\varepsilon_i(\lambda)$ are the above-stated physical parameters. $L_{eff}(\lambda)$ is an "effective path length", i.e. the average path length the light travels in the measuring cell in the gas mixture with the absorbers. While $L_0(\lambda)$ is the average path length during a calibration measurement, as explained above, $L_{eff}(\lambda)$ is the average path length during the measurement for determining the concentrations. The summand A is a parameter that can be freely selected during the curve fitting calculation and by which the device properties can be taken into account. Compared to the first-mentioned conventional method, this conventional method has the advantage that a variation of the light intensity emitted from the light source between the time of the initial measurement for deter mining the initial light intensity and the time of the actual measurement for determining the light intensity for the concentrations of the absorbing gases does not directly lead to a faulty curve fitting calculation, because due to the logarithmic expression of $M(\lambda)$, a variation by the factor q "is included" in the selectable summand A, since ln $$\left(\frac{I_0(\lambda)}{q * I(\lambda)}\right) = \ln\left(\frac{I_0(\lambda)}{I(\lambda)}\right) - \ln q.$$

However, in this conventional method, it problem to determine the effective path length $L_{eff}(\lambda)$, which physically depends on the concentrations of the absorbing gases themselves, as discussed above. Usually, this effective path length is approximated by assuming that $L_{eff}(\lambda) = L_0(\lambda) * K(\lambda)$, where $L_0(\lambda)$ represents the above described path length and $K(\lambda)$ represents a correction factor calculated using $$K(\lambda) = \frac{\ln\left(\frac{I_0(\lambda)}{I(\lambda)}\right)}{\frac{I_0(\lambda)}{I(\lambda)} - 1}.$$

Through this definition of the effective path length, the correctness of the fitting calculation becomes, however, again dependent on whether the state of the spectroscopic measuring device at the determination of $I_0(\lambda)$ was identical with the state at the determination of $I(\lambda)$, because only then it can be assumed that the determination of $K(\lambda)$ for the determination of the effective path length $L_{eff}(\lambda)$ is sufficiently correct. Through this calculation of $K(\lambda)$ from $I_0(\lambda)$ and $I(\lambda)$, which is usually applied, the method becomes mathematically equivalent to the above-mentioned representation of the measurement value function using $$M(\lambda) = \frac{I_0(\lambda)}{I(\lambda)} - 1,$$

which can be easily derived by substitution. For this reason, the correctness of the determined concentrations in the above-described conventional method for determining the concentrations of absorbing gases with a spectroscopic measuring device also essentially depends on the condition that the spectroscopic measuring device is kept constant during different measurements. This is complicated and can be hardly implemented free of errors so that even this method involves excessive cost and a high error rate. Additionally, in such methods, even in case of a—hypothetically—perfect match of the state of the measuring device during the two measurements for $I_0(\lambda)$ and $I(\lambda)$, the calculation of $K(\lambda)$ is always limited to an accuracy which is defined by the properties of the measuring device, especially the spectral resolution of the detector.

SUMMARY

It is an object of the present invention to provide a method for the determination of concentrations of absorbing gases in a gas mixture to be measured using a spectroscopic measuring device that allows a simple, inexpensive and error-free determination of the concentrations and particularly removes the above-described drawbacks of conventional methods. Further, it is an object of the present invention to provide a spectroscopic measuring device that can be manufactured at low cost and guarantees a preferably error-free determination of concentrations of absorbing gases in a measured gas mixture.

In the inventive method, the measured gas mixture is arranged in the measuring cell of a spectroscopic measuring device, which comprises the measuring cell, a light source, a detector and a computing unit. The measuring cell comprises an optical resonator. The inventive method serves to determine concentrations of absorbing gases contained in the measured gas mixture. Therefore, a light beam is emitted to the entrance of the measuring cell from a light source, and a detector, which is arranged outside of the measuring cell, determines a wavelength-dependent measurement value for a light intensity of light leaving from the exit of the measuring cell. The determination of a wavelength-dependent measurement value is accomplished in the form that the detector provides a measurement value for the light intensity and assigns this value to a particular wavelength.

The light source is able to emit light of different wavelengths. For example, the light source can be designed as a spectrally broadband light source that emits light in a wavelength range of at least 100 pin, particularly at least 1 nm, even more particularly at least 10 nm. The light source can be configured, for example, as a tunable laser which emit light in different wavelength ranges.

From the read-out values from the detector and thus determined measurement values, a wavelength-dependent shape of the light intensity describes the wavelength-dependent measurement value function. For example, the measurement value function can directly be depicted from the measurement values as $I(\lambda)$, where the measurement values $I_n$, which are each assigned to a particular derived wavelength $\lambda_n$ directly describe the shape $I(\lambda)$. For example, the measurement value function can be represented by $$\frac{I(\lambda)}{I_0(\lambda)} \text{ or } \ln\left(\frac{I(\lambda)}{I_0(\lambda)}\right),$$

where $I_0$ describes the wavelength-dependent shape of an initial light intensity that has been determined by the spectroscopic measuring device by read out of the detector during an initial measurement, in particular a calibration measurement, during which zero air with known properties was arranged in the measuring cell. For example, the measurement value function can be generally determined by multiplying the measured shape $I(\lambda)$ by a numerical value that may depend on the wavelength $\lambda$ or by adding it to such a numerical value. In any case, the measurement value function reflects the wavelength-dependent shape of the light intensity measured by the detector.

Further, in the method of this invention a theoretic wavelength-dependent function is defined by mathematically expressing the theoretically expected shape of the defined measurement value function on the basis of physical laws. Therein the concentrations of the absorbing gases are included in the theoretical function as freely selectable parameters. Depending on the application and according intended embodiment, a particular number of absorbing gases is assumed. It goes without saying that in a particularly simple embodiment, the method for determining the concentration is performed for only one absorbing gas so that the theoretical function then merely includes one concentration of the only one absorbing gas. In the subsequent description, particularly also of advantageous embodiments of the invention, reference is generally made to the term in "absorbing gas", hence to a particular quantity of absorbing gases which of course, can also be limited to only one absorbing gas, which accordingly simplify the advantageous embodiment of the invention. For the person skilled in the art, it goes without saying that correspondingly simplified arrangements according to the invention can be used, for example, in the case of a gas mixtures having a very simple composition or in the case of a light source having a very limited spectrum. In addition to the concentrations represented as a parameter, the theoretical function still depends on a wavelength-dependent calibration parameter by which the state of the measuring device during the measurement for determining the measurement values for the determination of the measurement value function is included. The definition of the theoretical function in dependence of such a calibration parameter is mandatory, due to the above-mentioned reasons for a basic structure of a spectroscopic measuring device comprising an optical resonator. In the method according to the invention, the curve fitting calculation between the theoretical function and the measurement value function is performed by adjusting at least the concentrations of the absorbing gases, which are contained as selectable parameters in the theoretical function, in order to approximate the theoretical function in its shape to the measurement value function as well as possible. In addition to the concentrations, the theoretical function can include further fit parameters to be adjusted, for example further extinction parameters, in which physical circumstances during the determination of the measurement values, i.e. during the measurement, can be taken into account. Such additional fit parameters are independent of the concentration of the absorbing gases and can be included in the theoretical function so that in the curve fitting calculation the approximation of the theoretical function to the measurement value function is as correct as possible and as error-free as possible.

According to the invention, for performing the curve fitting calculation, the calibration parameter is defined as a function of a predetermined wavelength-dependent device parameter and a wavelength-dependent correction factor, wherein the correction factor is defined as a function of the concentrations. As described above, in a particularly simple embodiment, the correction factor can be defined as a function of only one concentration of only one absorbing gas. Using this functional representation of the calibration parameter, the properties of the spectroscopic measuring device and especially the influences of the measuring cell of the measuring device on the measurement values for the light intensity can be taken into account particularly easily and also precisely. According to the invention the calibration parameter includes both, the condition of the measuring device, such as the reflectivity and the distance of the mirrors of the mirror assembly, and the shortening of the light path due to the extinction in the gas mixture. The device parameter can be obtained from a calibration measurement previously performed. For example, the device parameter can characterize a path length of the light which the light beam travels in the measuring cell. As a device parameter, for example a device path length can be determined, as explained above, in particular by carrying out a calibration measurement, or an average residence time or a reflectivity of the measuring cell can be determined as a device parameter. Through the correction factor, the change in the light propagation in the measuring cell caused by extinction is considered. In addition to the concentrations of the absorbing gases, the correction factor can also include one, in particular more than one additional extinction parameters, through which the other extinction effects are included, for example extinction effects due to Mie scatterers such as from aerosols and/or extinction effects of Rayleigh scattering such as for example from $N_2$. Particularly preferably, the correction factor is defined as a function, which at least depends on the following selectable parameters, the absorption cross sections known from literature and on the concentrations of the absorbing gases. Particularly preferably, the calibration parameter is defined as a product of the device parameter with the correction factor, whereby the calibration parameter can mathematically be formulated as simply as possible and physically as correctly as possible.

According to the method of the invention, a cycle comprising a sequence of steps is successively performed several times, wherein in a first step of the sequence a numerical value for the correction factor is calculated from stipulated assumed values of the concentrations using the function defining the correction factor. In a second step of the sequence, the theoretical function is determined, wherein the calibration parameter is calculated with the numerical value for the correction factor calculated in the first step. In a third step of the sequence, values for the concentrations are determined by means of a curve adjustment calculation between the theoretical function determined in the second step and the measurement value function and are set as new assumed values, wherein the determined assumed values in the third step of the last cycle are output as measurement values of the concentration. As numerical value for the correction factor, a highly resolved, wavelength-dependent numerical value is preferably provided in the first step. As described, in a particularly simple embodiment, in which the concentration of only one absorbing gas is determined, the correction factor can be calculated from a stipulated assumed value for this concentration in the first step, a new assumed value for this concentration can be determined in the third step, and the assumed value for this concentration determined in the third step of the last cycle can be output as the measured value for this concentration.

The method according to the invention makes it possible to perform a curve fitting calculation based on a mathematically highly complex and physically very accurate theoretical function. In this theoretical function, the concentrations are included, on the one hand, in the function defining the correction factor so that the calibration parameter is defined depending on the concentrations, in order to take account of the distribution or rather the light path of the light in the measuring cell during the measurement. On the other hand, the concentrations are included in another function part of the theoretical function which is independent of the calibration parameter and through which the absorption behavior of the gas mixture, in particular the included extinction behavior of the gas mixture, is described physically-mathematically. The theoretical function thus enables an extraordinarily correct theoretical representation of the expected measurement value. In prior art, such a theoretical function is not applied for carrying out a curve fitting calculation, since a direct curve fitting calculation between the measurement value function and the theoretical function by directly changing the concentrations numerically is not possible, since the functional dependency of the path length of the light path on the concentrations is too different from the functional dependency of the function part describing the absorption behavior of the gas mixture on the concentrations. This is the reason why the present invention takes a different approach: The curve fitting calculation is carried out in iterative cycles, wherein before the beginning of each cycle, the concentrations are respectively initially fixed to an assumed value, which is a numerical value and hence no freely selectable parameter in the curve fitting calculation. Thereafter, in a first step of each cycle, a numerical value for the correction factor is calculated by substituting the stipulated assumed values for the concentrations into the function defining the correction factor. In some embodiments, the correction factor cannot only be represented as a function of the concentrations of the absorbing gases, but also as a function of at least one additional extinction parameter, in order to account for additional extinction effects in the measuring cell that do not arise from the absorbing gases. Because extinction which shorten the path length the light travels in the measuring cell before it emerges from the measuring cell and hits on the detector, can for example not only be caused by absorption, but also by scattering. In these embodiments, also assumed values for this at least one additional extinction parameter are included in the function defining the correction parameter which are fixed as numerical values in the first step of each cycle. The second step can, for example, be performed chronologically after the first step. The second step can, for example, be performed simultaneously with the first step, for example, by substituting the stipulated assumed values directly into the theoretical function that includes the correction factor. It is always important that in the determination of the theoretical function, which is accomplished in the second step, the correction factor included in the theoretical function does not depend on adjustable concentrations as parameters, but the stipulated assumed values are substituted as concentrations into the correction factor or the function defining the correction factor.

Compared to conventional methods, two of which have been described above as exemplary methods, the method according to the invention makes it possible to take into account the change of the light path caused by extinction in the measuring cell, in a highly precise manner. The inventors have realized that the conventional methods take into account the shortening of the light path by extinction only within the limits of the measuring accuracy of the measuring device, in particular only within the limits of the typically low spectral resolution of the detector. This becomes particularly obvious if one looks at the above described prior art method in which an "effective path length" $L_{eff}(\lambda)$ is determined through $L_{eff}(\lambda)=L_0(\lambda)*K(\lambda)$ using $$K(\lambda) = \frac{\ln\left(\frac{I_0(\lambda)}{I(\lambda)}\right)}{\frac{I_0(\lambda)}{I(\lambda)} - 1}.$$

Because $K(\lambda)$ depends on $I(\lambda)$ and $I_0(\lambda)$, even depends non-linear, the determination of $L_{eff}(\lambda)$ is additionally distorted, if a gas mixture with absorbing gases contained in the measuring cell having a narrowband absorption structure whose half-width is less than or equal to the spectral resolution of the detector. Because the detector smoothes narrowband absorptions, due to its to low resolution of the measurement $I(\lambda)$ respectively $I_0(\lambda)$, and thus they appear weaker, which results in a falsify correction factor $K(\lambda)$. Compared to the conventional methods, the method according to the invention has the advantage that a very precise calculation of the correction factor at a high spectral resolution can be made, which is particularly not limited by the spectral resolution of the detector. Because, by formulating the correction factor mathematically-physically as a function of the concentrations, the correction factor can be defined with a very high spectral resolution for example, through the introduction of the spectrally high-resolution cross sections, known from literature, into the function defining the correction factor. In this case, high spectral resolution means a spectral resolution less than 0.5, but preferably less than 0.1 times the half-width value of the narrowband absorption structures of the absorber. Accordingly, compared to the conventional method, the method according to the present invention has a further advantage, that the correction factor can be very correctly determined even if the gas mixture in the measuring cell includes absorbing gases having narrowband absorption structures whose half-width value is less than or equal to the resolution of the detector. Generally, in this case, the usual methods considerably underestimate the correction factor. In particular, the method according to the present invention allows to determine concentrations of absorbing gases by means of a measuring device as quickly and precisely as possible while requiring as little computing power as possible. Moreover, by a suitable selection of the measurement value function and the theoretical function, the method according to the present invention can make it possible that the determination of concentrations of absorbing gases is not influenced by a variation of the operating state of the light source (e.g. a variation of the emitted light intensity), for example, by selecting the measurement value function M through $$M(\lambda) = \ln\left(\frac{I_0(\lambda)}{I(\lambda)}\right)$$

as described above. Because the method according to the invention inherently allows a precise characterization of the path length of the light path of the light beam in the measuring cell by carrying out the determination of the concentrations during the curve fitting calculation iteratively. Thus, a precise determination of the concentrations of the absorbing gases can be achieved by the selection of a corresponding measurement value function and a corresponding definition of a theoretical function, particularly one that is independent of an absolute intensity.

According to the invention, in a first step a numerical value for the correction factor is determined. In the second step of each cycle, the calibration parameter is calculated from this numerical value of the correction factor using a numerical value previously obtained for the device parameter during a calibration measurement. Accordingly, the calibration parameter obtained in the second step of each cycle is not dependent on the concentrations as freely selectable fitted parameters, since for the determination of the calibration parameters stipulated assumed numerical values are used for the concentrations. In an exemplary embodiment, the calibration parameter can be determined as a numerical value in the second step. It is generally preferred that a "calculation" as used in the present description, for example, the calculation of the correction factor from the assumed values during the first step and/or the calculation of the calibration parameter from the correction factor during the second step, is performed by a computer. For example, the calculation can be performed by an analytical or numerical calculation method based on the function defining the correction factor or the calibration parameter. For example, the calculation can be performed by storing in a memory of the computer, advance used values and values calculated from these values by means of a function so that when the method for determining the concentration is performed in the computer it is based on the value stored in the memory of the computer which is assigned to the inserted value, which were calculated in advance by applying the function and stored in the memory. In this manner, different correction factors assigned to different assumed values or different values for the calibration parameter assigned to different correction factors that have been previously obtained based on the function defining the correction factor or the calibration parameter in the computer, can be stored in such a memory, wherein in the computer, in the first step, the assigned correction factor, based on the stipulated assumed values, is retrieved from the memory respectively in the second step, the assigned calibration parameter based on the calculated correction factor is read from the memory. In one exemplary embodiment, the calibration parameter comprises in addition to a numerical value at least one additional compensation parameter, in which physical effects are combined in order to simplify the curve adjustment calculation in the third step of each cycle.

Then, in a third step of the cycle, a curve adjustment calculation is performed by a comparison between the theoretical function determined in the second step and the measurement value function, wherein, the concentrations included in the theoretical function as freely selectable parameters are adjusted, in order to adjust the theoretical function, which has been determined in the second step, as closely as possible to the measurement value function. Therefore, methods known in error measurement are used for the curve adjustment calculation, in order to reduce the remaining errors between the theoretical function and the measurement value function as far as possible by numerically adjusting the concentrations. In one embodiment, in which the function part describing the absorption property of the gas mixture comprises in addition to the concentrations of the absorbing gases further extinction parameters for characterizing the gas mixture, also these extinction parameters can be adjusted in addition to the concentrations in the third step, in order to approximate the theoretical function to the measurement value function as well as possible. In the third step, the values output for the concentrations from the completed curve compensation calculation are stipulated as new assumed values. In embodiments, in which the theoretical function includes at least one additional extinction parameter as further fit parameters to be adjusted, new assumed values are stipulated in the third step also for these additional extinction parameters. Thereafter, the cycle is repeated in a next iteration, wherein the assumed values for the concentrations and particularly for the additional extinction values obtained in the third step of the previous cycle are used as stipulated assumed values. Thus, in the subsequent cycle, for determining a numerical value for the correction factor in the first step, assumed values are used that have been obtained by means of the curve adjustment calculation of the previous cycle. Accordingly, it can be assumed that these assumed values of the subsequent cycle are closer to the real values of the concentrations in the gas mixture than the assumed values in the previous cycle. By the iterative repetition of the cycle, a stepwise approximation of the assumed values of the concentrations determined in the curve adjustment calculation of the respective cycle to the real concentration values in the gas mixture is achieved. In some embodiments, simultaneously a stepwise approximation of the values of the extinction parameters to the real values in the gas mixture is achieved by the iterative repetition. By the fact that the functional dependency of the correction factor on the concentrations and in particular on further extinction parameters as adjustable parameters is not considered during the curve adjustment calculation, the method according to the invention avoids a comparison between an excessively complex function and the measurement value function which is de facto numerically not feasible. The method according to the invention rather enables a stepwise approximation of the assumed values for the concentrations to the real concentration values in the gas mixture, whereby any curve adjustment calculation becomes numerically feasible and the entire curve fitting calculation can be accomplished based on the theoretical function, which is physically formulated very accurately.

Particularly preferably, during the curve adjustment calculation of each cycle, the concentrations and in particular further extinction parameters as parameters of the theoretical function are changed in order to reduce the differences between the theoretical function and the measurement value function. Continuously changing the concentrations and particularly the further extinction parameters of the theoretical function in each cycle guarantees from cycle to cycle a continuous optimization of the agreement between the theoretical function and the measurement value function, which is accompanied by a continuously improved approximation of the concentrations determined in the respective curve adjustment calculation of the respective cycle to the concentrations of the absorbing gases really prevailing in the gas mixture. In this case, it must be taken into account that due to this continuous change of both the further extinction parameters and the concentrations, a preferably comprehensive adjustment of the complexly formulated theoretical function can be accomplished, whereby a preferably error-free determination of the concentrations can be guaranteed.

In one embodiment, the device parameter is obtained by a calibration measurement using the measuring device, wherein the measured values of the concentrations of absorbing gases are obtained by the curve fitting calculation based on measurement values obtained in a measurement that is carried out separately from the calibration measurement. Accordingly, the calibration measurement is performed using the same spectroscopic measuring device as the one used for the measurement carried out for obtaining the measurement values for the determination of the concentrations of the absorbing gases by the curve fitting calculation. In terms of time, the calibration measurement can be carried out before or after the measurement for obtaining the above-mentioned measurement values. For example, the calibration measurement can be carried out while zero air is provided in the measuring cell, for example air that has been filtered by aerosol filters and/or other filters serving to remove absorbing gases, for example zero air in the form of $N_2$, $O_2$ or an $N_2O_2$ mixture. In any case, the calibration measurement serves to determine a numerical value of the device parameter that is substituted into the theoretical function when the curve fitting calculation for determining the concentrations from the measurement values obtained during the measurement is performed.

In one embodiment, the theoretical function is defined as a sum of a first summand, which depends on the calibration parameter and on a function part that physically-mathematically describes exclusively narrowband absorption characteristics of the gas mixture and is defined depending on the concentrations as a parameter to be fitted, and a second summand, which is defined as broadband parameter that is independent of the concentrations and of the calibration parameter. This embodiment enables a fast and inexpensive determination of the concentrations of absorbing gases in the gas mixture at a low computational effort. In particular embodiments, in this case, only concentrations of such absorbing gases are determined, which have a narrowband absorption structure, which applies, however, for a variety of relevant trace gases. A narrowband absorption structure can, for example, be defined by the fact that when the absorption structure is observed through a measurement of the light intensity, the wavelength-dependent measurement values obtained, cannot be approximated by a polynomial $\leq 3^{rd}$ order with the error between this polynomial and the wavelength-dependent shape of the measurement values being smaller than the measurement error during the measurement. The described embodiment makes it possible to formulate the function part of the theoretical function describing the absorption property of the gas mixture mathematically, considering only physical laws that describe a narrowband absorption. Thus, the theoretical function can have a simpler formulation, which results in a correspondingly simpler curve adjustment calculation. Particularly preferably, the calibration parameter, which is included in the first summand, is defined as a function of the concentrations of the narrowband absorbing gases and as a function of further extinction parameters, through which also a broadband extinction is taken into account. This can enable a determination of the concentrations of the narrowband absorbing gases still simple, but even more precise, since taking into account also broadband extinction effects in the calibration parameter, accounts for its caused change of the light path in the measuring cell.

In an implementation of this embodiment, the broadband parameter is determined independently of the curve fitting calculation from the measurement value function itself and is then substituted into the theoretical function during the curve fitting calculation. For example, such a determination of the broadband parameter from the measurement value function can be performed by calculating a smoothing of the measurement value function by taking an average of two values of the measurement value function that are assigned to two wavelengths, which are separated from each other by a fixed wavelength spacing. As such a fixed wavelength separation for example 1 nm, for example 5 nm, can be selected. The smoothing is calculated from the measurement value function by always setting for the entire wavelength range between the two wavelengths assigned values of the measurement value function the calculated average value. Alternatively, the broadband parameter can be determined for example from the measurement value function from a fitting calculation carried out prior to the curve adjustment calculation. In such a fitting calculation, the measurement value function is first approximated with a $3^{rd}$ order polynomial (i.e. a polynomial $$P = \sum_{i=0}^{3} v_i * \lambda^i,$$

with the parameters to be fitted $v_i$) by fitting the polynomial parameters $v_i$. Since the broadband parameter can be substituted into the curve fitting calculation as a constant numerical value, the curve adjustment calculation can be performed particularly easily. In another implementation of the above-mentioned exemplary embodiment, the broadband parameter is included in the theoretical function by the definition as a $n^{th}$ order polynomial $$\left(P = \sum_{i=0}^{N} v_i * \lambda^i\right)$$

in the theoretical function, wherein the parameters $v_i$ are also fitted along with the curve adjustment calculation at the same time. In this case, $N \leq 5$, in particular $\leq 3$, is chosen, since this allows broadband effects to be approximated sufficiently well and thus to keep the number of polynomial parameters $v_i$ small, so that the compensation calculation is easier to perform. Additionally, the selection of a correspondingly low degree of the polynomial guarantees that the polynomial does not describe a narrowband extinction effect, but describes exclusively broadband effects. Thus, it can be ensured that the determination of the concentration during the curve fitting calculation is not distorted by the inclusion of the broadband parameter.

In one embodiment, the calibration parameter in the physical-mathematical formulation of the theoretical function is selected so that it characterizes an average path length of a light path of the light in the measuring cell, wherein the theoretical function is defined based on a representation of the light intensity $I(\lambda)$ as $I(\lambda) = I_0(\lambda) \cdot \exp(-L \cdot \varepsilon)$, where $I_0(\lambda)$ is the light intensity of the leaving light when a gas mixture without or with a known extinction property is arranged in the measuring cell, L is the calibration parameter and $\varepsilon$ is an extinction property of the gas mixture to be measured that depends on the concentration of the absorber gases, wherein the determination of the theoretical function is accomplished in the second step by specifying numerical values for the cross sections and the device parameters and by substituting the concentrations as parameters to be fitted. Accordingly, in this embodiment, the theoretical function is described based on the known Beer-Lambert law, which has been recognized as a physically exact definition of the theoretical function. By this formulation of the theoretical function, it is assumed that $I(\lambda)$ is the light intensity to be physically expected, which is read out from the detector during the measurement, whereas $I_0(\lambda)$ is an initial light intensity. This initial light intensity can be determined, for example, during a calibration measurement in which a pre-defined zero air is provided in the measuring cell. In the formulation of the theoretical function, L is the calibration parameter, which takes into account the state of the measuring cell during the measurement, whereas $\varepsilon$ includes the function part of the theoretical function, which takes into account the absorption property of the gas mixture. $\varepsilon$ depends on both, the concentrations and the cross sections of the absorbing gases. $\varepsilon$ can take into account both narrowband and broadband extinctions, such as for instance absorption and/or scattering effects. For example, $\varepsilon$ cannot only depend on the concentrations of the absorbing gases, but also on further extinction effects. The cross sections on which $\varepsilon$ depends, are known in the relevant literature and can thus be inserted as numerical values during the second step for determining the theoretical function so that $\varepsilon$ includes, for example, exclusively the concentrations of the absorbing gases as selectable parameters and in particular the concentrations of scattering gases as additional extinction parameters.

In one embodiment, an effective device path length $L_{eff}$ is used as a calibration parameter, where a path length $L_0$ is used as a device parameter, where $L_{eff}$ is represented as a product $L_{eff}(\lambda) = L_0(\lambda) * K(\lambda)$, where particularly $K(\lambda)$ is represented as $$K(\lambda) = \frac{D_{CE}(\lambda)}{\exp(D_{CE}(\lambda)) - 1},$$

where $D_{CE}$ is represented as $$D_{CE}(\lambda) = \ln\left(1 + L_0(\lambda)\left(\sum_{i=1}^{G} x_i \cdot \sigma_i(\lambda) + f\left(\vec{m}, \lambda\right)\right)\right),$$

where $x_i$ represents the stipulated assumed values of the concentrations of the absorbing gases and $\sigma_i$ represents the pre-known cross sections of the absorbing gases, wherein different absorbing gases G are assumed, where $f(\vec{m}, \lambda)$ describes a broadband attenuation of the light in the measuring cell, where $\vec{m}$ describes the quantity of extinction parameters $m_n$. It goes without saying that the method can be performed for a selectable number G of different absorbing gases and, in a particularly simple embodiment, also for only one absorbing gas (G=1). The described embodiment simultaneously allows a physically precise formulation of the theoretical function and performing a compensation calculation during the third step of each cycle, since the parameterization of the theoretical function through the parameters $x_i$ and $\vec{m}$ to be fitted during the curve adjustment calculation is still simple enough to enable a numerical adaption of these freely selectable parameters during the curve adjustment calculation. The calibration parameter is defined depending on the device parameter $L_0$, the concentrations $x_i$ and the cross sections $\sigma_i(\lambda)$ of the absorbing gases and depending on the extinction parameters (through the function $f(\vec{m},\lambda)$). For both the concentrations $x_i$ and also for the extinction parameters $m_n$, the quantity of extinction parameters of $\vec{m}$, assumed values are stipulated prior to the first step, through which the theoretical function is defined during the second step. In the third step, both the extinction parameters $m_n$, the quantity of extinction parameters of $\vec{m}$, and the concentrations $x_i$ of the absorbing gases are varied during the curve adjustment calculation. In one embodiment of the inventive method, the function $f(\vec{m},\lambda)$ is defined through $f(\vec{m},\lambda)=\varepsilon_{Mie}(\vec{m}_1,\lambda)+\Delta\varepsilon_{Rayleigh}(\vec{m}_2,\lambda)$. This is based on the physical principle that the broadband attenuation of the light in the measuring cell is mainly based on Mie scattering and Rayleigh scattering at corresponding scatterers. The extinction parameter vector $\vec{m}$, which describes the quantity of extinction parameters, comprises the extinction parameters $m_n$ that are included in the two different extinction parameter vectors $\vec{m}_1$ and $\vec{m}_2$. In one embodiment, the function $f(\vec{m},\lambda)$ is defined as a low-order polynomial, in particular a polynomial of the order ≤5, in particular a polynomial of the order ≤3, in the theoretical function, i.e.

$$f(\vec{m},\lambda) = \sum_{n=0}^{N} m_n * \lambda^n.$$

In one embodiment, the function $f(\vec{m},\lambda)$ is approximated by a power function $f(\vec{m},\lambda)=m_1*\lambda^{m_2}$, where the extinction parameters $m_1$ and $m_2$ represent the parameters to be adjusted during the curve adjustment calculation. When $f(\vec{m},\lambda)$ is represented as a power function, the curve adjustment calculation can be carried out particularly easily, since merely two extinction parameters $m_1$ and $m_2$ need to be adjusted. Such an approximation for the function $f(\vec{m},\lambda)$ can be physically useful and can lead to a very precise determination of the concentrations by applying the inventive method, especially if it is guaranteed that the gas mixture to be measured contains no different Rayleigh scatterers, but exclusively Miescatterers, compared to the zero-air provided in the measuring cell during the measurement of the initial intensity for the determination of $I_0(\lambda)$.

In one embodiment, in a first intermediate step during the second step, for each absorbing gas a specific wavelength-dependent theoretical absorption shape is calculated from the calculated calibration parameter and a pre-known cross section of the respective absorbing gas. In a second intermediate step during the second step, a theoretical absorber spectrum is calculated for each absorbing gas by a mathematical convolution of the respective absorption profile with a predetermined instrument function. The theoretical function is defined as a function of the absorber spectra of the respective absorbing gases as wavelength-dependent numerical values and of the concentrations of the absorbing gases as parameters. In this embodiment, the theoretical function is physically particularly exactly defined, since the respective absorption profile of the respective absorbing gas, in which the wavelength-dependent calibration parameters of the measuring device and the wavelength-dependent cross section of the respective absorbing gas are included, is mathematically convoluted with the instrument function in order to define a theoretical absorber spectrum, which then identifies for each absorbing gas the absorber spectrum depending on the concentration that is theoretically expected and measurable with the measuring device. In this case, it must be taken into account, that both the calibration parameter and the cross section very strongly depend on the wavelength so that the mathematical convolution of the absorption shape determined with the instrument function is of significant importance for the physically preferably exact determination of the theoretical function. Due to the fact that according to the invention for the calibration parameter a value is defined in each iterative cycle, which is independent of the concentrations as adjustable parameters, even with the mathematical convolution it can be guaranteed in the method according to the invention that the theoretical function, through which the curve adjustment calculation is performed in the third step of each cycle, is still formulated simple enough (depending on the concentrations and in particular on additional extinction parameters) so that the curve adjustment calculation can be carried out numerically. At this point it is generally noted that the instrument function is a function that takes into account the characteristics of the measuring behavior of the spectroscopic measuring device, particularly of the detector. For example, the sensitivity of the detector and the resolution of the detector relative to the wavelength are taken into account.

In a particularly preferred embodiment, the calibration parameter is calculated using $$L_{eff}(\lambda) = L_0(\lambda) * K(\lambda) = L_0(\lambda) * \frac{D_{CE}(\lambda)}{\exp(D_{CE}(\lambda))-1},$$

where $$D_{CE}(\lambda) = \ln\left[1 + L_0(\lambda)\left(\sum_{i=1}^{G} x_i \sigma_i(\lambda) + f(\vec{m},\lambda)\right)\right],$$

where $L_{eff}(\lambda)$ represents the calibration parameter, $L_0(\lambda)$ represents the device parameter, $\sigma_i$ represents the cross section of a particular absorbing gas and $x_i$ the stipulated assumed value of the particular absorbing gas, wherein G different absorbing gases are assumed, $f(\vec{m},\lambda)$ represents a broadband attenuation of light in the measuring cell and $\vec{m}$ the quantity of extinction parameters. This embodiment describes a mathematically simple and also precise formulation of the calibration parameter and hence determination of the theoretical function so that the curve adjustment calculation in the third step of each cycle can be performed in a manner with reduced error, so that the concentrations of the absorbing gases in the gas mixture can be determined as exactly as possible. It goes without saying that the method can be performed for a selectable number G of different absorbing gases and, in a particular simple embodiment, also for only one absorbing gas (G=1). The inventors have realized that the use of spectrally highly resolved $\sigma_i(\lambda)$ is particularly advantageous for an exact determination of $L_{eff}(\lambda)$, since this can particularly contribute to a correct determination of $L_{eff}(\lambda)$ which is not limited by the resolution of the detector and that even narrowband absorption structures whose half-value width is less than or equal to the resolution of the detector can be correctly taken into account.

Particularly preferably, the mathematical convolution for the determination of the absorber spectrum of the particular absorbing gas is performed based on the equation $$\Theta_i(\lambda) = \frac{1}{x_i} \ln\left[H(\lambda) \otimes e^{-L_{eff} * \sigma_i(\lambda) * x_i}\right],$$

where $\Theta_i(\lambda)$ is the absorber spectrum of the particular absorbing gas and $H(\lambda)$ is the instrument function, in a particular approximation of this equation, the convolution is performed with the approximated equation $\Theta_i(\lambda)=H(\lambda)\otimes(L_{eff}(\lambda)*\sigma_i(\lambda))$. Here $H(\lambda)$ is the pre-known instrument function of the optical measuring device, in particular under consideration of the properties of the detector of the measuring device. Through the described convolution, the absorber spectra $\Theta_i(\lambda)$ can be physically exactly determined and the absorber spectra can be subsequently used in the second step of each cycle for the determination of the theoretical function. The absorber spectra $\Theta_i(\lambda)$ can be approximated particularly exactly by the approximation $\Theta_i(\lambda)=H(\lambda)\otimes(L_{eff}(\lambda)*\sigma_i(\lambda))$, if it can be assumed that the gas mixture contains no strong absorbing gases having absorption structures which, in relation to the wavelength, are much narrower relative to the resolution of the detector of the measuring device. The inventors have realized that through the mentioned approximation, which can be applied in a large number of gas mixtures, the performed curve adjustment calculation can even be more simplified so that the concentrations can be determined faster and at lower cost using the method according to the invention.

In one embodiment, the theoretical function T is calculated from the absorber spectra in the second step of each cycle as follows: It is assumed that the theoretical function can be defined as function T, which depends on the concentrations $\vec{x}$, the extinction parameters $\vec{m}$ and the polynomial parameters $\vec{v}$. Correspondingly, in this embodiment, the theoretical function is defined as $$T = T(\vec{x}, \vec{m}, \vec{v}, \lambda) = \sum_{i=1}^{G} \Theta_i(\lambda) \cdot x_i + H(\lambda) \otimes [L_{eff}(\lambda) \cdot f(\vec{m}, \lambda)] + P(\vec{v}, \lambda),$$

where $\vec{x}$ is used to represent the quantity of different concentrations $x_i$, each of which is assigned to one of the various absorbing gases. In the present case, G different absorbing gases are assumed so that $\vec{x}$ contains G different $x_i$. $\vec{m}$ describes the quantity of extinction parameters and $\vec{v}$ describes a quantity of polynomial parameters. In a preferred form of embodiment of the described embodiment, the summand of the theoretical function $H(\lambda)\otimes\lfloor L_{eff}(\lambda)*f(\vec{m},\lambda)\rfloor$ is approximated by: $H(\lambda)\otimes\lfloor L_{eff}(\lambda)*f(\vec{m},\lambda)\rfloor=L_{eff}(\lambda)*f(\vec{m},\lambda)$. By this approximation, the theoretical function can continue to reflect the measure value function physically-mathematically extremely precisely, since the wavelength dependence on $L_{eff}(\lambda)*f(\vec{m},\lambda)$ is relatively small in relation to the resolution of the detector, which is included in the instrument function $H(\lambda)$. $P(\vec{v},\lambda)$ describes a broadband parameter through which a broadband extinction property of the gas mixture in the measuring cell is taken into account. In the described embodiment, the broadband parameter is adjusted along with the curve adjustment calculation as a parameter independent of $\vec{x}$ and $\vec{m}$. In this case, $P(\vec{v},\lambda)$ can be defined, for example, as $$P(\vec{v}, \lambda) = \sum_{i=0}^{N} v_i \lambda^i.$$

Accordingly, P is defined as a polynomial, wherein preferably $N\leq 5$, particularly $N=3$, is set for the definition of the theoretical function, since a sufficiently good approximation to a broadband absorption spectrum can be achieved by a corresponding polynomial while the number of parameters to be adjusted during the curve adjustment calculation can be kept small. As explained above, for example also $f(\vec{m},\lambda)$ can be represented as a J-order polynomial, i.e.

$$f(\vec{m}, \lambda) = \sum_{n=0}^{J} m_n \lambda^n,$$

for example, as a polynomial with $J\leq 5$, in particular as a polynomial with $J=3$, hence a $3^{rd}$ order polynomial so that in this case four extinction parameters ($m_0$, $m_1$, $m_2$, $m_3$) are included in the vector defining the quantity of extinction parameters $\vec{m}$. It will be apparent to a person skilled in the art that in the described embodiment a theoretical function T is defined, in which all parameters to be adjusted are contained linearly. This formulation of a theoretical function, which exclusively linearly depends on the parameters to be adjusted during the curve adjustment calculation, is generally very advantageous because it enables a preferably simple implementation of the curve adjustment calculation and hence an error-minimizing approximation of the theoretical function to the measurement value function. This embodiment shows that the method according to the invention with cycles performed iteratively, actually enables a preferably error-minimizing curve fitting calculation based on physically very exactly formulated theoretical functions in the first place. This is because the iterative process guarantees that the parameters to be adjusted, which are contained in the calibration parameter ($L_{eff}(\lambda)$ in the described embodiment), do not appear in complex functional dependencies in the theoretical function during the definition of the theoretical function, which would make it practically impossible to perform a curve adjustment calculation. As shown in the exemplary embodiment, it is rather the iterative process, which makes it possible that no complex dependencies of the theoretical functions on the parameters to be adjusted arise, even if a convolution for determining the theoretical function is carried out. This is based on the fact that the functions that have to be convoluted with the instrument function can be kept simple, because during the convolution, the parameters to be adjusted are only contained as numerical values in the calibration parameter.

In one embodiment, the number of cycle which are performed in a row are defined by a) predefining a number of cycles and stipulating it, when the maximal number of cycles is reached, no further cycle is performed, b) stipulating that no further cycle is performed as soon as the assumed values obtained in the most recent cycle differ from the assumed values obtained in the previous cycle by less than a limit value for all concentrations and/or c) stipulating that no further cycle is performed as soon as a residuum between the measurement value functions and the theoretical function obtained in the most recent cycle by setting the assumed values is less than a predetermined threshold. In some embodiments, only one of the three stated options of the stipulation can be accomplished, in other embodiments two or all three of the stated options are combined. In this case, it can be stipulated that no further cycle is performed as soon as one condition of the conditions mentioned in the three options is achieved. Concerning option a), an absolute maximal number of cycles is predetermined, after which no further cycle is performed. Concerning option b), the assumed values obtained in the third step of a particular cycle are stored and compared with the assumed values obtained in the third step of the subsequent cycle. Particularly, option b) can be defined in such a manner that no further cycle is performed only if the assumed values obtained in the most recent cycle are different from the assumed values obtained in the previous cycle for the respective parameters by less than a limit value for all parameters of the theoretical function to be adjusted during the curve adjustment calculation, i.e. for all concentrations, and particularly for additional parameters to be adjusted, such as the extinction parameter and especially the polynomial parameter. As a limit value there can be set for example a fixed value for each parameter to be adjusted, in particular a common limit value for all concentrations. For example, also a percentage difference between the assumed value of the respective parameter in the most recent cycle and the assumed value of the respective parameter in the previous cycle can be set as a limit value. For example, the limit value can be set also dependent on an error value of the fit that is determined during the curve adjustment calculation and describes the quality of the match of the theoretical function obtained in the curve adjustment calculation with the measurement value function. Concerning option c), it can be defined that a residuum between the measurement value function and the theoretical function obtained in the third step that describes the degree of match of the theoretical function with the measurement value function is determined for each cycle during the third step. No further cycle is performed if the residuum is lower than a predetermined threshold.

Particularly preferably, the assumed values of the concentration are respectively set to a particular numerical value prior to performing a first cycle, wherein the respective particular numerical value is read out from a memory of the measuring device or is manually input by a user, and wherein the measurement value of the respective concentration obtained in a previous measurement is particularly used as the respective particular numerical value. The particular numerical value can be fixed in an arbitrary manner, being identical with 0 for example, in order to provide an identical starting point for each measurement from which the cycles are iteratively performed. For example, the numerical value can also be manually input by a user, and the user can choose the particular numerical value corresponding to his expectation of the presumed concentrations in the gas mixture. In this manner, the duration of the process for obtaining the concentrations can be shortened, since one starts from a realistic first assumed value, which allows reducing the number of iterations necessary to achieve a correct assumed value for the concentrations or the output of the correctly measurement values for the concentrations. For example, the particular numerical value input by the user or the numerical value read out from the memory can be the numerical value obtained as a measurement value of the respective concentrations in a previous measurement. If the previous measurement was carried out under comparable conditions, i.e. on a comparable gas mixture, this also makes it possible to reduce the number of iterations and hence shorten the duration of the invented method, until preferably exact values for the concentrations are obtained.

In one embodiment, the gas mixture is filtered by means of an aerosol filter before it reaches the measuring cell. In this manner, it is possible to substantially exclude an extinction property of the gas mixture in the measuring cell, which is based on Mie scattering. In this manner, the formulation of the theoretical function can be simplified, which leads to that the method according to the invention can be carried out at lower cost and more quickly. For example, the above-stated function for taking into account broadband extinction properties of the gas mixture $f(\vec{m},\lambda)$ can be written in a simplified form as $f(\lambda)=\Delta\varepsilon_{Rayleigh}(\lambda)$, where $\Delta\varepsilon_{Rayleigh}(\lambda)$ can be calculated as the further extinction parameter using the Rayleigh scattering cross sections known in the relevant literature and the density of the gas mixture, if the pressure and the temperature in the gas mixture are known. In this manner, the theoretical function can be defined without the need to substitute further parameters as parameters to be adjusted into the theoretical function. In this manner, the number of parameters to be adjusted during the curve fitting adjustment can be reduced so that the concentrations of the absorbing gases in the gas mixture can be determined more quickly and more precisely.

The invention also relates to a spectroscopic measuring device that comprises a light source, a measuring cell comprising an optical resonator, a detector and a computing unit. The light source is configured for emitting a light beam, which enters a measuring cell through an entrance along a light path and emerges from the measuring cell through an exit. The detector is located outside of the measuring cell at the exit of the measuring cell and is configured for deriving wavelength-dependent measurement values for a light intensity of the light which hit the detector. The computer unit is configured to read out measurement values from the detector and to represent a wavelength-dependent shape of the light intensity as a wavelength-dependent measurement value function. The computer unit is further configured to obtain concentrations of absorbing gases present in the gas mixture provided in the measuring cell using a curve fitting calculation between a theoretical wavelength-dependent function and the wavelength-dependent measurement value function, wherein the theoretical function comprises a wavelength-dependent calibration parameter for taking into account the state of the measuring device as well as the concentrations as parameters to be adjusted during the curve fitting calculation. According to the invention, the computer unit is designed to perform a process for obtaining the concentrations under definition of the calibration parameter as a function of a wavelength-dependent device parameter stored in the computer unit, and a wavelength-dependent correction parameter defined as a function of the concentrations, the computer unit being configured for performing a cycle comprising a sequence of steps, wherein a) in a first step of the sequence, a numerical value for the correction factor is calculated from stipulated assumed values of the concentrations using the function defining the correction factor, b) in a second step of the sequence, the theoretical function is determined, wherein the calibration parameter is calculated from the numerical value for the correction factor calculated in the first step, c) in a third step of the sequence, values for the concentrations are obtained by a curve adjustment calculation between the theoretical function determined in the second step and the measurement value function and are stipulated as new assumed values, wherein the computer unit is configured to perform the cycle several times in a row and output the assumed values obtained in the third step of the last cycle as measured values of the concentrations, i.e. measurement values of the concentrations. The spectroscopic measuring device according to the invention can be manufactured at low cost while enabling a very precise determination of concentrations of absorbing gases in a gas mixture. As described above, this is because the concentrations can be determined based on precisely formulated physical equations so that no complicated stabilization measures are needed, such as a stabilization of the light intensity of the light source of the measuring device as required in conventional spectroscopic measuring devices in which strongly approximated physical equations are used for obtaining the concentrations that require corresponding stabilizing measures of the spectroscopic device, which is due to the configuration of the spectroscopic measuring device and especially the computer unit of the measuring device. In particular, the spectroscopic measuring device according to the invention enables still a determination of the concentrations with very low error even if the light intensity emitted from the light source varies by more than 10% between a calibration measurement for calibrating the measuring device to enable a data analysis of the measurement values, in particular for determining the device parameter, and the actual measurement for determining the concentrations.

In one embodiment, the measuring cell is designed as a measuring cell sealed in a gas tight manner against the surrounding area, wherein the measuring cell comprises an entrance for the entry of the gas mixture into the measuring cell, and wherein an aerosol filter is disposed at the entrance to filter aerosols from the gas mixture reaching the measuring cell. This embodiment makes it possible to prevent a Mie scattering in the measuring cell during the measurement at least as far as possible or even completely. In this manner, functions for determining the concentrations can be stored in the computer unit, which are mathematically formulated less complex and which are physically formulated very exactly so that it is possible to determine the concentrations exceptionally quickly and accurately.

The spectroscopic measuring device according to the present invention may comprise further features and advantages that will become apparent from the following description of the method according to the invention and the various embodiments of the method according to the invention.

BRIEF DESCRIPTION OF THE DRAWINGS

In the following, the invention will be described in more detail by exemplary embodiments with reference to attached drawings comprising three Figures. They show.

DETAILED DESCRIPTION

Figure 1A:
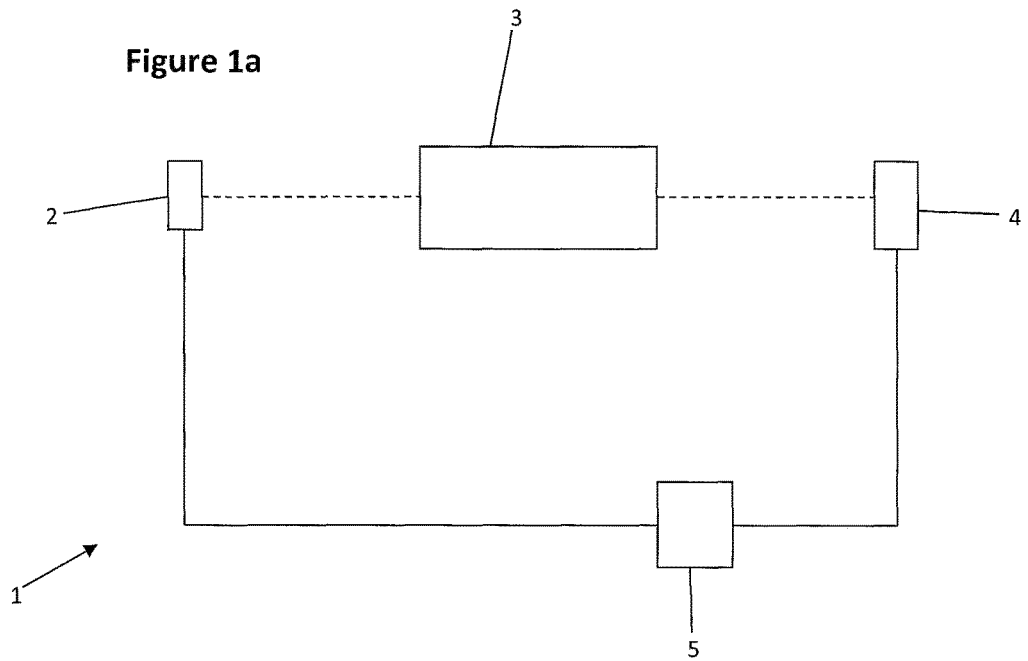
FIGS. 1a and 1b are simplified schematic representations of the structure of a measuring device according to the invention.

FIG. 1a shows the basic structure of one embodiment of a spectroscopic measuring device 1 according to the invention. The spectroscopic measuring device 1 comprises a light source 2, in the present case configured as a LED, a measuring cell 3, a detector 4 and a computing unit 5. In the spectroscopic measuring device 1 according to FIG. 1a, the light source 2, the computing unit 5 and the detector 4 are electrically connected to each other, which is shown by the solid lines in FIG. 1. Further, in FIG. 1, the path of a light beam from the light source 2 to the detector 4 is shown purely schematically by a broken line. The basic concept of spectroscopic measuring devices 1 becomes clear from FIG. 1a: A light source 2 emits a light beam, which enters into the measuring cell 3 of the spectroscopic measuring device 1 through an entrance, passes an optical light path and leaves the measuring cell 3 at the exit, from where it hits on a detector 4. The detector 4 thus measures the light intensity of the light that has been emitted from the light source 2 and has passed the measuring cell 3.

Figure 1B:

Furthermore, FIG. 1b shows the basic structure of a measuring cell 3 used in spectroscopic measuring device 1 according to FIG. 1a in a schematic representation. The measuring cell 3 includes a mirror assembly comprising a first mirror 31 and a second mirror 32. The first mirror 31 simultaneously represents the entrance of the measuring cell 3, and the second mirror 32 represents the exit of the measuring cell 3. Light which is coupled into the measuring cell 3 via the first mirror 31, is reflected several times backwards and forwards between the first mirror 31 and the second mirror 32, wherein each time light hits on the mirror 32, a portion of the light is decoupled from the second mirror 32. The light decoupled from the second mirror 32, i.e. the light leaving from the exit of the measuring cell 3, is guided by basic optical components like lenses to a detector 4 on which the decoupled light hit, i.e. the light leaving from the exit, wherein the detector 4 outputs the light intensity of the light which hit thereon as a measurement value depending on the wavelength. The measurement values output from the detector 4, are recorded and evaluated in the computing unit 5 to determine the concentrations of absorbing gases in the gas mixture that is arranged in the measuring cell 3 of the spectroscopic measuring device 1. Particularly from FIG. 1b it is apparent that the path length the light travels in the measuring cell 3 depends on both the reflectivity of the mirror assembly in the measuring cell 3 and the extinction properties of the gas mixture in the measuring cell 3. Accordingly, the average path length the light travels in the measuring cell 3 before leaving the measuring cell 3 at the exit becomes shorter if a gas mixture with strong absorption properties is arranged in the measuring cell 3, since in this case, the light is absorbed by the gas mixture before it can be very frequently reflected backwards and forwards between the mirrors 31, 32 of the measuring cell 3.

In the measuring device 1 according to the invention, the computing unit 5 is configured to represent a wavelength-dependent measurement value function from the measurement values the computing unit 5 reads out from the detector 4 and determine concentrations of absorbing gases using a curve fitting calculation between a theoretical wavelength-dependent function and the wavelength-dependent measurement value function. In this case, the computer unit 5 is configured in such a manner that it defines a theoretical function as a function of a wavelength-dependent calibration parameter in order to take into account the state of the measuring device. In this case, the computing unit 5 is configured to perform the determination of the concentrations under definition of the calibration parameter as a function of a wavelength-dependent device parameter stored in the computing unit 5 and a wavelength-dependent correction factor defined as a function of the concentrations, wherein the computing unit is configured to perform a cycle comprising a sequence of steps, wherein a) in a first step of the sequence, a numerical value for the correction factor is calculated from stipulated assumed values using the function defining the correction factor, b) in a second step of the sequence, the theoretical function is determined, wherein the calibration parameter is calculated from the numerical value calculated in the first step for the correction factor, c) in a third step of the sequence, values for the concentrations are obtained by a curve adjustment calculation between the theoretical function determined in the second step and the measurement value function and are set as new assumed values, wherein the computing unit 5 is configured to perform the cycle several times in a row and output the assumed values obtained in the third step of the last cycle as measurement values of the concentrations.

Figure 2:
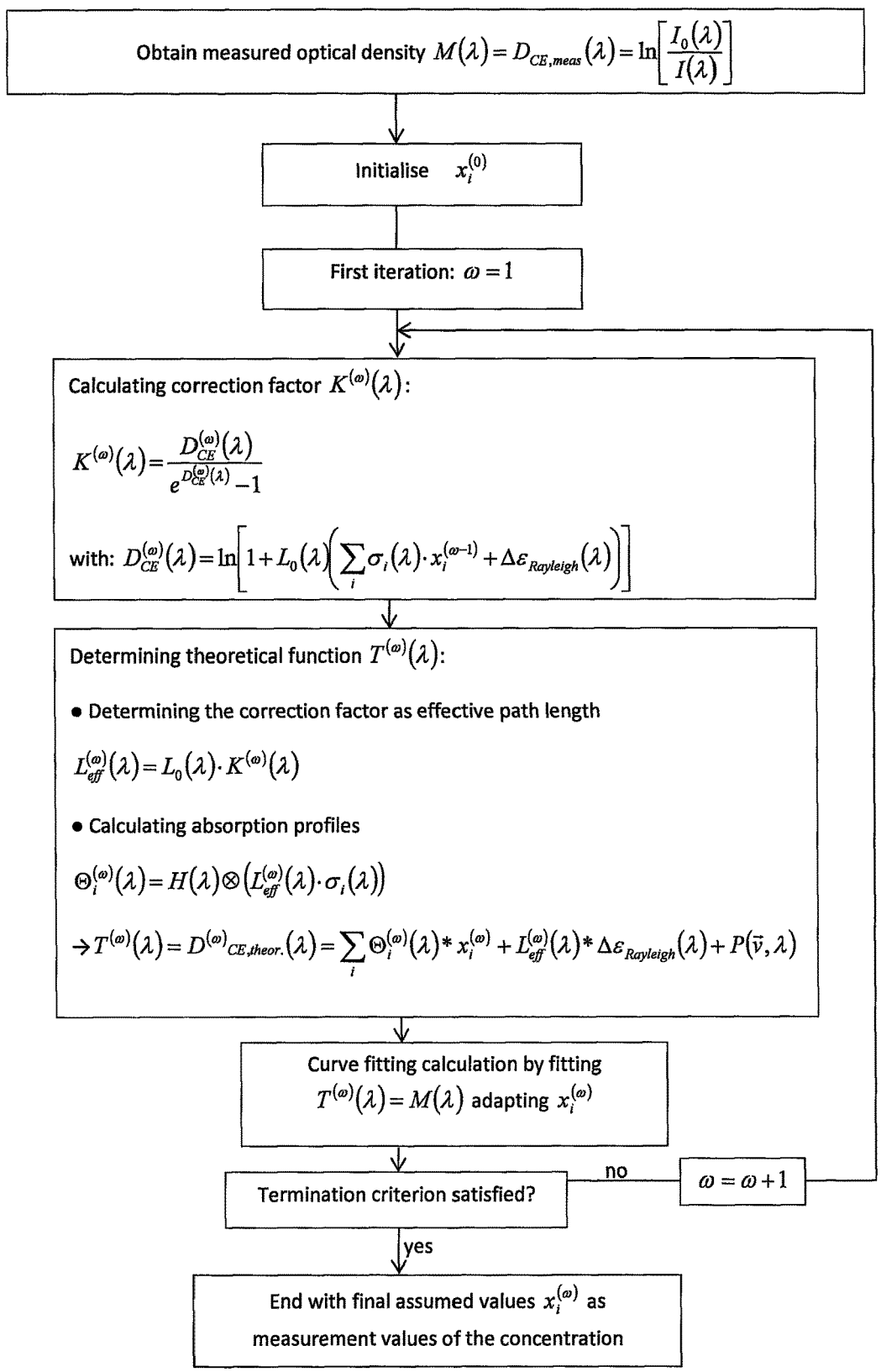
FIG. 2 is a flow diagram for illustrating the flow of one embodiment of a method according to the invention.

FIG. 2 schematically shows in a flowchart the various steps, which are performed by the computer unit 5 of the spectroscopic measuring device 1 and which correspond to the steps of a corresponding embodiment of a method according to the invention in the determination of concentrations of absorbing gases. First of all, the computing unit 5 obtains a wavelength-dependent measurement value function $M(\lambda)$ from the measurement values read out from the detector 4. In the present exemplary embodiment, it is defined as a measurement value function of the optical density $D_{CE,meas}(\lambda)$ using $$M(\lambda) = D_{CE,meas}(\lambda) = \ln\left[\frac{I_0(\lambda)}{I(\lambda)}\right].$$

In this case, $I(\lambda)$ is the wavelength-dependent shape of the measurement values of the light intensity read out from the detector 4 during the measurement, whereas $I_0(\lambda)$ is the wavelength-dependent shape of the measurement values during an initial measurement in which zero air is arranged in the measuring cell, in the present case nitrogen ($N_2$). $I_0(\lambda)$ has been obtained during an initial measurement carried out prior to the measurement for determining the concentrations of the absorbing gases in the gas mixture and thus represents an initial light intensity. $I_0(\lambda)$ is stored in the computer unit 5. Thereafter, the assumed values for the concentrations $x_i$ are respectively set to an initial value denoted $x_i^{(0)}$ in FIG. 2, before a first cycle is performed. In the described exemplary embodiment, this initial value is read out from a memory in the computing unit 5 in which the value for the concentrations $x_i$ obtained in the previous measurement is stored. This value from the previous measurement is set as an initial value $x_i^{(0)}$. Then the cycle is performed several times in a row. During each cycle, the stipulated assumed value ($x_i^{(0)}$ in the first cycle) is first inserted as a numerical value for the respective concentrations, from which the correction factor $K^{(\omega)}(\lambda)$ is determined using corresponding mathematical equations and the calibration parameter $L_{eff}^{(\omega)}(\lambda)$ for the cycle $\omega$ is determined using the correction factor. This calibration parameter, which in the present case is defined as an effective path length, is then used for determining the theoretical function. In the described exemplary embodiment, the absorber spectra $\Theta_i^{(\omega)}(\lambda)$ are first determined for each particular absorbing gas i, thereafter the theoretical function is determined through $$T^{(\omega)}(\lambda) = D_{CE,theor.}^{(\omega)}(\lambda) = \sum_i \Theta_i^{(\omega)}(\lambda) * x_i^{(\omega)} + L_{eff}^{(\omega)}(\lambda) * \Delta\varepsilon_{Rayleigh}(\lambda) + P(\vec{v}, \lambda),$$

where $$P(\vec{v}, \lambda) = \sum_j v_j * \lambda^j.$$

In this case, it must be taken into consideration that in the described embodiment the spectroscopic measuring device 1 has an entrance for allowing gas to enter into the measuring cell 3, and an aerosol filter is disposed at the entrance to filter aerosols from the gas mixture reaching the measuring cell 3 so that the Mie scattering in the measuring cell 3 can be neglected in the formulation of the theoretical function T. In the described exemplary embodiment, $\Delta\varepsilon_{Rayleigh}(\lambda)$ is mathematically calculated by measuring the temperature and the pressure by means of corresponding sensors of the spectroscopic measuring device 1 and by reading Rayleigh scattering cross sections from a memory in the computing unit 5. Accordingly, in the described exemplary embodiment, the theoretical function exclusively contains the concentrations $x_i$ of the absorbing gases as parameters to be fitted. Subsequently, a curve adjustment calculation between measurement value functions $M(\lambda)$ and the theoretical function $T^{(\omega)}(\lambda)$ is performed in the same cycle $\omega$, wherein the concentrations $x_i^{(\omega)}$ are changed in order that the theoretical function is adapted to the measurement value function as well as possible. After performing the curve adjustment function, a determination is made whether another cycle is performed. To this end, a termination criterion is determined and it is checked whether the termination criterion is satisfied. In the present case, the termination criterion is defined when no further cycle $\omega+1$ is performed, if the assumed values $x_i^{(\omega)}$ obtained in the most recent cycle $\omega$ differ from the assumed values $x_i^{(\omega-1)}$ obtained in the previous cycle $\omega-1$ by less than 2%. If the termination criterion is not satisfied, another cycle $\omega+1$ is performed, wherein the assumed values $x_i^{(\omega)}$ for the determination of the correction factor are substituted into this cycle $\omega+1$. Once the termination criterion is satisfied, the assumed values $x_i^{(\omega)}$ obtained in the last cycle are output as measurement values of the concentration.

Figure 3:
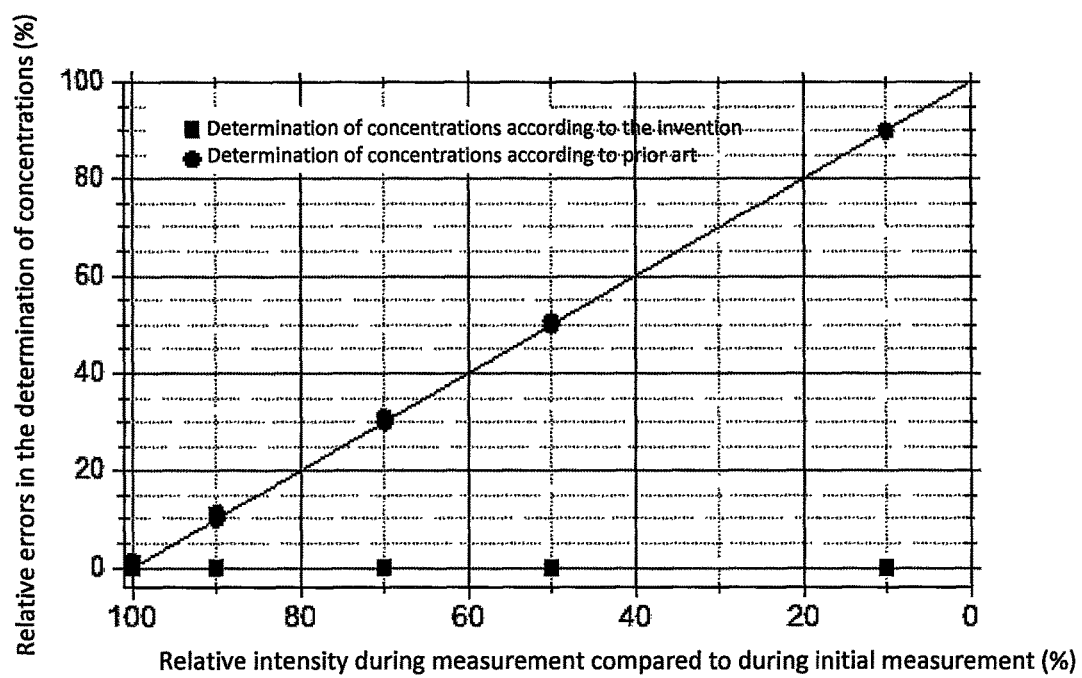
FIG. 3 is a schematic representation of the low susceptibility to errors of the method according to the invention compared to conventional methods.

FIG. 3 shows an essential advantage of the method according to the invention or the spectroscopic measuring device 1 according to the invention. In FIG. 3, the relative errors in the determination of the concentrations are represented in dependence on a relative variation of the intensity of the light emitted from the light source 2 of the spectroscopic measuring device 1 which takes place between an initial measurement for obtaining $I_0(\lambda)$ and the actual measurement carried out for obtaining $I(\lambda)$ in the described exemplary embodiment according to the FIGS. 1 and 2. These relative errors of the spectroscopic measuring device 1 according to the invention are represented along with the relative errors of a conventional measuring device 1, in which the light source 2 presents corresponding variations of the light intensity. In FIG. 3, the relationship between the intensity of the light emitted from the light source during the measurement for the determination of $I_0(\lambda)$ and the light intensity emitted from the light source during the actual measurement for the determination of $I(\lambda)$ is indicated on the X-axis. It can be clearly seen in FIG. 3 that a determination of the concentration of absorbers in the gas mixture in the measuring cell 3 can still be performed with a very small error with the inventive spectroscopic measuring device 1 even if the light intensity varies considerably. This is, however, not possible for conventional spectroscopic measuring devices. Due to this reason conventional spectroscopic measuring devices require a complex, expensive and mostly not completely satisfying stabilization of the light intensity emitted from the light source 2 of the measuring device 1 and a stabilization of the optical system.

Accordingly, it becomes apparent from the described exemplary embodiments that the spectroscopic measuring device 1 according to the invention or the method according to the invention enables an error-free determination of concentrations of absorbing gases in a gas mixture without requiring complex measures to be taken for stabilizing the measuring device 1 during measurements being performed.

LIST OF REFERENCE NUMBERS

1 spectroscopic measuring device
2 light source
3 measuring cell
4 detector
5 computing unit
31 first mirror
32 second mirror

What is claimed is:

1. A method for determining at least one concentration of at least one absorbing gas in a gas mixture to be measured by means of a spectroscopic measuring device, which comprises a light source, a measuring cell comprising an optical resonator, a detector and a computer unit, wherein the gas mixture is arranged in the measuring cell and a light beam is sent to the measuring cell through an entrance of the measuring cell by means of the light source, wherein wavelength-dependent measurement values for a light intensity of light leaving from an exit of the measuring cell are obtained by means of the detector, wherein a wavelength-dependent shape of the light intensity is represented as a wavelength-dependent measurement value function and wherein a curve fitting calculation between a theoretical wavelength-dependent function and the wavelength-dependent measurement value function is performed, wherein the theoretical function contains a wavelength-dependent calibration parameter for taking into account the state of the measuring device as well as at least one concentration of the at least one absorbing gas contained in the gas mixture as a parameter to be fitted during the curve fitting calculation, wherein for performing the curve fitting calculation, the calibration parameter is defined as a function of a predetermined wavelength-dependent device parameter and a wavelength-dependent correction factor, wherein the correction factor is defined as a function of at least one concentration, wherein a cycle comprising a sequence of steps is performed several times in a row, wherein
a) in a first step of the sequence, a numerical value for the correction factor is calculated from a stipulated assumed value for the at least one concentration using the function defining the correction factor;
b) in a second step of the sequence, the theoretical function is determined, wherein the calibration parameter is calculated from the numerical value for the correction factor calculated in the first step; and
c) in a third step of the sequence, a value of the at least one concentration is obtained by a curve adjustment calculation between the theoretical function determined in the second step and the measurement value function and is stipulated as new assumed value for the concentration, wherein the assumed value obtained in the third step of the last cycle is output as a measured value of the at least one concentration;

wherein
an effective path length $L_{eff}$ is used as a calibration parameter, wherein a device path length $L_0$ is used as a device parameter, wherein $L_{eff}$ is represented as a product $L_{eff}(\lambda)=L_0(\lambda)*K(\lambda)$, wherein in particular $K(\lambda)$ is represented as $$K(\lambda) = \frac{D_{CE}(\lambda)}{\exp(D_{CE}(\lambda)) - 1},$$

wherein $D_{CE}$ is represented as $$D_{CE}(\lambda) = \ln\left[1 + L_0(\lambda)\left(\sum_{i=1}^{G} x_i * \sigma_i(\lambda) + f(\vec{m}, \lambda)\right)\right],$$

wherein $x_i$ represents the stipulated assumed values of the concentrations of the absorbing gases and $\sigma_i$ represents pre-known cross sections of the absorbing gases, wherein G different absorbing gases are assumed, wherein $f(\vec{m},\lambda)$ describes a broadband attenuation of the light in the measuring cell, wherein $\vec{m}$ is the quantity of extinction parameters $m_n$.

2. The method according to claim 1, wherein during the curve adjustment calculation, the at least one concentration as a parameter of the theoretical function is changed to reduce the differences between the theoretical function and the measurement value function.

3. The method according to claim 1, wherein the device parameter is obtained by a calibration measurement using the measuring device, wherein the measured value of the at least one concentration of the at least one absorbing gas is obtained by the curve fitting calculation which is based on measurement values obtained in a measurement performed separately from the calibration measurement.

4. The method according to claim 1, wherein the theoretical function is defined as a sum of a first summand, which depends on the calibration parameter and a function part that exclusively describes narrowband absorption properties of the gas mixture and is defined in dependence on the at least one concentration as a parameter to be adjusted, and a second summand that is defined as a broadband parameter being independent of the at least one concentration and the calibration parameter.

5. The method according to claim 1, wherein the calibration parameter is selected to characterize a path length of a light path of the light in the measuring cell, wherein the theoretical function is defined based on a representation of the light intensity $I(\lambda)$ as $I(\lambda)=I_0(\lambda)\cdot\exp(-L\cdot\varepsilon)$, where $I_0(\lambda)$ is the light intensity of the leaving light when a gas mixture without or with a known extinction property is arranged in the measuring cell, L is the calibration parameter and $\varepsilon$ is an extinction property of the gas mixture to be measured, which depends on the at least one concentration of the at least one absorbing gas and the at least one cross section of the at least one absorbing gas, wherein the determination of the theoretical function in the second step is accomplished by predetermining numerical values for the at least one cross section and the device parameter and by using the at least one concentration as a parameter to be adjusted.

6. The method according to claim 1, wherein during a first intermediate step of the second step, a specific wavelength-dependent theoretical absorption shape is calculated from the calculated calibration parameter and a pre-known cross section of the respective absorbing gas wherein in a second intermediate step, a theoretical absorber spectrum is calculated for each absorbing gas by a convolution of the respective absorption shape with a predetermined instrument function, wherein the theoretical function is defined as function of the absorber spectra of the respective absorbing gases being a wavelength dependent number of numerical values and as function of the concentrations of the respective absorber gases as parameters.

7. The method according to claim 6, wherein the calibration parameter is calculated using $$L_{\textit{eff}}(\lambda) = L_0(\lambda) * K(\lambda) = L_0(\lambda) * \frac{D_{CE}(\lambda)}{\exp(D_{CE}(\lambda))-1},$$

wherein $$D_{CE}(\lambda) = \ln\left[1 + L_0(\lambda)\left(\sum_{i=1}^{G} x_i\sigma_i(\lambda) + f(\vec{m},\lambda)\right)\right],$$

where $L_{\textit{eff}}(\lambda)$ is the calibration parameter, $I_0(\lambda)$ is the device parameter, $\sigma_i$ is the cross section of a particular absorbing gas and $x_i$ is the stipulated assumed value of the particular absorbing gas, wherein G different absorbing gases are assumed, wherein $f(\vec{m},\lambda)$ is a broadband attenuation of light in the measuring cell and $\vec{m}$ is the quantity of extinction parameters.

8. The method according to claim 7, wherein the mathematical convolution for determining the absorber spectrum of the particular absorbing gas is performed based on the equation $$\Theta_i(\lambda) = \frac{1}{x_i}\ln\left[H(\lambda)\otimes e^{-L_{\textit{eff}}*\sigma_i(\lambda)*x_i}\right],$$

where $\Sigma_i(\lambda)$ represents the absorber spectrum of the particular absorbing gas and $H(\lambda)$ represents the instrument function, wherein in particular, as an approximation of this equation, the convolution is performed using the approximated equation $\Theta_i(\lambda)=H(\lambda)\otimes(L_{\textit{eff}}(\lambda)*\sigma_i(\lambda))$.

9. The method according to claim 1, wherein the number of cycles which are performed in a row are defined according to:
 a) predefining a maximum number of cycles and defining that no further cycle is performed once the maximum number of cycles is reached;
 b) stipulating that no further cycle is performed as soon as the assumed values obtained in the most recent cycle are different from the assumed values obtained in the previous cycle by less than a limit value for all concentrations; and/or
 c) stipulating that no further cycle is performed as soon as a residuum between the measurement value function and the theoretical function determined in the most recent cycle by setting the assumed values is less than a predetermined threshold.

10. The method according to claim 1, wherein the at least one assumed value of the at least one concentration is respectively fixed to a particular numerical value prior to performing a first cycle, wherein the respective particular numerical value is read out from a memory of the measuring device or is manually input by a user, wherein in particular the measured value of the respective concentration obtained in a previous measurement is used as the respective particular numerical value.

11. The method according to claim 1, wherein the gas mixture is filtered by an aerosol filter before reaching the measuring cell.

12. A spectroscopic measuring device, comprising a light source, a measuring cell comprising an optical resonator, a detector and a computing unit, wherein the light source is configured for emitting a light beam which enters through an entrance into the measuring cell along a light path and emerges from the measuring cell through an exit, wherein the detector is arranged outside of the measuring cell at the exit and configured to output a wavelength-dependent measurement value for a light intensity of light which hit thereon, wherein the computing unit is configured to read out the measurement values from the detector and to represent a wavelength-dependent shape of the light intensity as a wavelength-dependent measurement value function and also to determine the concentration of at least one absorbing gas using a curve fitting calculation between a theoretical wavelength-dependent function and the wavelength-dependent measurement value function, wherein the theoretical function includes a wavelength-dependent calibration parameter for taking into account the state of the measuring device and at least one concentration of the at least one absorbing gas contained in the gas mixture as parameters to be adjusted during the curve fitting calculation,
 wherein
 the computing unit is configured to perform the determination of the concentration of at least one absorbing gas under definition of the calibration parameter as a function of a wavelength-dependent device parameter stored in the computing unit and a wavelength-dependent correction factor defined as a function of the at least one concentration, wherein the computing unit is configured to perform a cycle comprising a sequence of steps, wherein
 a) in a first step of the sequence, a numerical value for the correction factor is calculated from a stipulated assumed value for the at least one concentration using the function defining the correction factor;

b) in a second step of the sequence, the theoretical function is determined, wherein the calibration parameter is calculated from the numerical value for the correction factor calculated in the first step; and c) in a third step of the sequence, a value for the at least one concentration is obtained by a curve adjustment calculation between the theoretical function determined in the second step and the measurement value function and is used as a new assumed value for the at least one concentration, wherein the computing unit is configured to perform the cycle several times in a row and output the assumed value obtained in the third step of the last cycle as a measured value of the at least one concentration, wherein an effective path length $L_{eff}$ is used as a calibration parameter, wherein a device path length $L_0$ is used as a device parameter, wherein $L_{eff}$ is represented as a product $L_{eff}(\lambda)=L_0(\lambda)*K(\lambda)$, wherein in particular $K(\lambda)$ is represented as $$K(\lambda) = \frac{D_{CE}(\lambda)}{\exp(D_{CE}(\lambda))-1},$$

wherein $D_{CE}$ is represented as $$D_{CE}(\lambda) = \ln\left[1 + L_0(\lambda)\left(\sum_{i=1}^{G} x_i * \sigma_i(\lambda) + f(\vec{m},\lambda)\right)\right],$$

wherein $x_i$ represents the stipulated assumed values of the concentrations of the absorbing gases and $\sigma_i$ represents pre-known cross sections of the absorbing gases, wherein G different absorbing gases are assumed, wherein $f(\vec{m},\lambda)$ describes a broadband attenuation of the light in the measuring cell, wherein $\vec{m}$ is the quantity of extinction parameters $m_n$.

13. The spectroscopic measuring device according to claim 12, wherein the measuring cell is designed as a measuring cell sealed in a gastight manner against the surroundings, wherein the measuring cell has an entrance allowing the gas mixture to enter into the measuring cell, wherein an aerosol filter for filtering out aerosols from the gas mixture reaching the measuring cell is disposed at the entrance.

14. A spectroscopic measuring device, comprising a light source, a measuring cell comprising an optical resonator, a detector and a computing unit, wherein the light source is configured for emitting a light beam which enters through an entrance into the measuring cell along a light path and emerges from the measuring cell through an exit, wherein the detector is arranged outside of the measuring cell at the exit and configured to output a wavelength-dependent measurement value for a light intensity of light which hit thereon, wherein the computing unit is configured to read out the measurement values from the detector and to represent a wavelength-dependent shape of the light intensity as a wavelength-dependent measurement value function and also to determine the concentration of at least one absorbing gas using a curve fitting calculation between a theoretical wavelength-dependent function and the wavelength-dependent measurement value function, wherein the theoretical function includes a wavelength-dependent calibration parameter for taking into account the state of the measuring device and at least one concentration of the at least one absorbing gas contained in the gas mixture as parameters to be adjusted during the curve fitting calculation, wherein the computing unit is configured to perform the determination of the concentration of at least one absorbing gas under definition of the calibration parameter as a function of a wavelength-dependent device parameter stored in the computing unit and characterizing a path length of the light which the light beam travels in the measuring cell as well as a wavelength-dependent correction factor defined as a function of the at least one concentration, wherein the computing unit is configured to perform a cycle comprising a sequence of steps, wherein a) in a first step of the sequence, a numerical value for the correction factor is calculated from a stipulated assumed value for the at least one concentration using the function defining the correction factor;

b) in a second step of the sequence, the theoretical function is determined, wherein the calibration parameter is calculated from the numerical value for the correction factor calculated in the first step; and c) in a third step of the sequence, a value for the at least one concentration is obtained by a curve adjustment calculation between the theoretical function determined in the second step and the measurement value function and is used as a new assumed value for the at least one concentration, wherein during the curve adjustment calculation the at least one concentration included in the theoretical function as freely selectable parameter is adjusted in order to adjust the theoretical function, which has been determined in the second step, as closely as possible to the measurement value function, wherein the computing unit is configured to perform the cycle several times in a row and output the assumed value obtained in the third step of the last cycle as a measured value of the at least one concentration.

15. A method for determining at least one concentration of at least one absorbing gas in a gas mixture to be measured by means of a spectroscopic measuring device, which comprises a light source, a measuring cell comprising an optical resonator, a detector and a computer unit, wherein the gas mixture is arranged in the measuring cell and a light beam is sent to the measuring cell through an entrance of the measuring cell by means of the light source, wherein wavelength-dependent measurement values for a light intensity of light leaving from an exit of the measuring cell are obtained by means of the detector, wherein a wavelength-dependent shape of the light intensity is represented as a wavelength-dependent measurement value function and wherein a curve fitting calculation between a theoretical wavelength-dependent function and the wavelength-dependent measurement value function is performed, wherein the theoretical function contains a wavelength-dependent calibration parameter for taking into account the state of the measuring device as well as at least one concentration of the at least one absorbing gas contained in the gas mixture as a parameter to be fitted during the curve fitting calculation, wherein for performing the curve fitting calculation, the calibration parameter is defined as a function of a predetermined wavelength-dependent device parameter characterizing a path length of the light which the light beam travels in the measuring cell and a wavelength-dependent correction factor, wherein the correction factor is defined as a function of at least one concentration, wherein a cycle comprising a sequence of steps is performed several times in a row, wherein:

a) in a first step of the sequence, a numerical value for the correction factor is calculated from a stipulated assumed value for the at least one concentration using the function defining the correction factor;

b) in a second step of the sequence, the theoretical function is determined, wherein the calibration parameter is calculated from the numerical value for the correction factor calculated in the first step; and c) in a third step of the sequence, a value of the at least one concentration is obtained by a curve adjustment calculation between the theoretical function determined in the second step and the measurement value function and is stipulated as new assumed value for the concentration, wherein during the curve adjustment calculation the at least one concentration included in the theoretical function as freely selectable parameter is adjusted in order to adjust the theoretical function, which has been determined in the second step, as closely as possible to the measurement value function, wherein the assumed value obtained in the third step of the last cycle is output as a measured value of the at least one concentration.

* * * * *